United States Patent [19]

Cohen et al.

[11] Patent Number: 5,525,470
[45] Date of Patent: Jun. 11, 1996

[54] METHOD OF SEQUENCING [SHORT] OLIGONUCLEOTIDES

[75] Inventors: Aharon S. Cohen, Brookline; Alexei Belenky, Newton; Christopher M. Ott, Oakham, all of Mass.

[73] Assignee: Hybridon, Inc., Worcester, Mass.

[21] Appl. No.: 187,749

[22] Filed: Jan. 26, 1994

[51] Int. Cl.$^6$ ...................................... C12Q 1/68
[52] U.S. Cl. ............... 435/6; 435/91.1; 435/91.2; 435/810; 436/501; 436/63; 536/22.1; 536/23.1; 536/24.1; 536/24.3; 536/24.31; 536/24.32; 536/24.33; 935/77; 935/78; 935/88
[58] Field of Search ..................... 435/6, 91.1, 91.2, 435/810; 436/501, 63; 536/22.1, 23.1, 24.1, 24.3–.33; 935/77, 78, 88

[56] References Cited

U.S. PATENT DOCUMENTS 5,403,709  4/1995  Agrawal et al. .................... 435/6

OTHER PUBLICATIONS

Maxam et al. (1977) *Proc. Natl. Acad. Sci.* (USA) 74:560–564.
Righetti et al. (1977) *J. Chromatog.* 137:171–181.
Sanger et al. (1977) *Proc. Natl. Acad. Sci.* (USA) 74:5463–5467.
McBride et al. (1983) *Tetrahedron Lett.* 24:245.
Artoni et al. (1984) *Anal. Biochem.* 137:420–428.
Dovichi et al. (1984) *Anal. Chem.* 56:348–354.
Vecchio et al. (1984) *Anal. Biochem.* 137:410–419.
Smith (1985) *Nucl. Acid. Res.* 13:2399–2412.
Smith et al. (1986) *Nature* 321:674–679.
Tessier et al. (1986) *Anal. Biochem.* 158:171–178.
Prober et al. (1987) *Science* 238:336–341.
Cheng et al. (1988) *Science* 242:562–564.
Cohen et al. (1988) *Chromotog.* 458:323–333.
Cohen et al. (1988) *Proc. Natl. Acad. Sci.* (USA) 85:9660–9663.
Lee (1988) *J. Chromatog.* 457:267–278.
Agrawal et al. (1990) *J. Chromotog.* 509:396–399.
Ansorge et al. (1990) *Nucleic Acids Res.* 18:3419–3420.
Cohen et al. (1990) *J. Chromotog.* 516:49–60.
Guttman et al. (1990) *Anal. Chem.* 62:137–141.
Swerdlow et al. (1990) *Nucl. Acids Res.* 18:1415–1418.
Tabor et al. (1990) *J. Biol. Chem.* 265:8322–8328.
Uhlmann et al. 1990 *Chem. Rev.* 90:543–583.
Huang et al. (1992) *Anal. Chem.* 64:2149–2154.
Nordhoff et al. (1992) *Rapid. Comm. Mass. Spectrom.* 6:771–776.
Pentoney et al. (1992) *Electrophoresis* 13:467–474.
Cohen et al. (1993) *TRAC* 12:195–202.
Keough et al. (1993) *Rapid. Comm. Mass. Spectrom.* 7:195–200.
Wu et al. (1993) *Rapid Comm. Mass. Spectrom.* 7:142–146.
Smith (1989) *Am. Biolab.* May: 10–25.
Tang et al. (1993) *Anal. Biochem.* 212:134–137.

*Primary Examiner*—W. Gary Jones
*Assistant Examiner*—Ardin H. Marschel
*Attorney, Agent, or Firm*—Lappin & Kusmer

[57]  ABSTRACT

Disclosed is a method for determining the nucleotide sequence of a target oligonucleotide. In this method a single-stranded ligation product is prepared which contains a target oligonucleotide-to-be sequenced and an auxiliary oligonucleotide. A primer complementary to a portion of the auxiliary oligonucleotide and having a label covalently attached thereto is annealed to the auxiliary oligonucleotide portion of the ligation product. The primer is extended with chain-extending nucleoside triphosphates and chain-terminating nucleoside triphosphates in the presence of a polymerase to yield a plurality of primer extension products. These extension products are then separated on the basis of their base length; and the nucleoside sequence of the target oligonucleotide is determined from the mobilities of the primer extension products obtained during their separation.

17 Claims, 8 Drawing Sheets

METHOD OF SEQUENCING [SHORT] OLIGONUCLEOTIDES

FIELD OF THE INVENTION

The invention relates to the characterization of oligonucleotides, and more particularly, to methods of determining the nucleotide sequence of oligonucleotides and oligonucleotide analogs.

BACKGROUND OF THE INVENTION

Nucleotide sequence determination is an important step in the analysis of a short strand of an unknown oligonucleotide or oligonucleotide analog and to confirm the specific sequence of oligonucleotides used as antisense drugs. At the present, most sequencing protocols use the chemical degradation approach of Maxam et al. (*Proc. Natl. Acad. Sci.* (USA) (1977) 74:560) or the chain-termination method of Sanger et al. (*Proc. Natl. Acad. Sci.* (USA) (1977) 74:5463). In these methods, four separate reactions are performed to yield fragments differing in length by only a single nucleotide which terminate at adenosine, cytosine, guanosine, or thymidine residues.

These sequencing products are generally resolved by electrophoresis on denaturing polyacrylamide gels (PAGE). High performance capillary electrophoresis (HPCE) has also been used to separate oligonucleotide sequencing products (Cohen et al. (1988) *J. Chromatogr.* 458:323; Cohen et al. (1988) *Proc. Natl. Acad. Sci.* (USA) 85:9660; Guttman et al. (1990) *Anal. Chem.* 62:137; Cohen et al. (1990) *J. Chromatogr.* 516:49; Cohen et al., *Anal. Chem.* (in press)), and can be readily coupled to mass spectrometry (Smith et al. (1988) *Anal. Chem.* 60:1948; Lee et al. (1988) *J. Chromatogr.* 457:313). However, traditionally, the method of product visualization has been autoradiography wherein $^{32}P$ or $^{35}S$ is incorporated into the oligonucleotide strand.

Recently, sequencing with laser-induced fluorescence (LIF) as a detection mode has been used in a variety of Sanger et al.-related protocols. In the basic method, four unique fluorescent tags are attached either to the primer (Smith et al. (1986) *Nature* 321:674) or to each of the terminating dideoxynucleotides (Prober et al. (1987) *Science* 238:336). In other Sanger et al.-related protocols, single-dye-based coding of bases with four different peak heights has been used (Tabor et al. (1990) *J. Biol. Chem.* 265:8322–8326; Ausorge et al. (1990) *Nucleic Acids Res.* 18:3419–3420; Pentoney et al. (1992) *Electrophoresis* 13:461–474); Huang et al. (1992) *Anal. Chem.* 64:2149–2154), as well as single-dye-based coding of bases by peak height ratios plus one base coded by a gap (Ausorge et al. (1990) *Nucleic Acids Res.* 18:3419–3420; Pentoney et al. (1992) *Electrophoresis* 13:461–474), and two-dye-binary coding of three bases with one base coded by a gap or two optical channels (Carson et al., *Anal. Chem.* (in press)).

Unfortunately, many oligonucleotides and oligonucleotide analogs such as those useful for the antisense chemotherapeutic approach are too short to be sequenced by conventional sequencing methodologies. For example, if one uses the Sanger et al. approach to sequence a short (e.g., 15 to 17 bases in length), single-stranded DNA, the base sequence at its 3' end is lost. The loss of information is primer size-dependent and normally 15 to 17 bases, i.e, sequence information will be provided right after the primer only.

Nevertheless, correct sequences are required for efficacy, and quality control procedures are needed to ensure that synthetic oligonucleotides have the desired nucleotide sequences. At present, the sequences of such oligonucleotides are often assumed to be correct based on the step-by-step synthesis itself since there is no convenient method available for their sequence analysis.

Enzymatic sequencing of short DNA analogs has been documented (Nordhoft et al. (1992) *Rapid Comm. Mass. Spectrom.* 6:771; Wu et al. (1993) *Rapid Comm. Mass. Spectrom.* 7:142; and Rile et al. (1993) *Rapid Comm. Mass. Spectrom.* 7:195). This method uses exonucleases with phosphodiester-linked DNA as a substrate and MALDI-MS for detection. The current protocol is relatively slow, as aliquots are taken every 15 minutes and directly analyzed by MALDI-MS (Tabor et al. (1990) *J. Biol. Chem.* 265:8322–8326). In addition, when DNA analogs are sequenced under these conditions, exonuclease digestion is very problematic and sometimes impossible.

An added level of complexity is the presence of modifications in oligonucleotides including non-phosphodiester linkages such as phosphorothioates or alkylphosphonates. Previous method of analyzing such oligonucleotide analogs have been laborious for commercial application. For example, Agrawal et al. (*J. Chromatogr.* (1990) 509:396–399) discloses analysis of oligonucleotide phosphorothioates involving conversion of phosphorothioate linkages to phosphodiesters followed by digestion with snake venom phosphodiesterase, phosphatase treatment, and analysis of base composition on reversed phase HPLC.

Thus, there remains a need for more simple and reliable methods of determining the sequence of short oligonucleotides and oligonucleotide analogs from their very first to their very last base.

SUMMARY OF THE INVENTION

The present invention provides an efficient and reliable method for determining the nucleotide sequence of short oligonucleotides and oligonucleotide analogs. Generally, conventional methods for determining nucleotide sequences are difficult to use for many oligonucleotides and synthetic oligonucleotides because such molecules are too short to serve as an efficient template. The method according to the invention overcomes this problem by providing a sequencing-length oligonucleotide that includes the target oligonucleotide-to-be-sequenced which is long enough to serve as an efficient template.

Target oligonucleotides capable of being sequenced by the method of the invention are composed of ribonucleotides, deoxyribonucleotides, analogs of ribonucleotides, analogs of deoxyribonucleotides, and combinations thereof. Thus, in some embodiments, the target oligonucleotides are synthetic or modified oligonucleotides or oligonucleotide analogs.

As used herein, the term "oligonucleotide" includes polymers of two or more ribonucleotide and/or deoxyribonucleotide monomers covalently linked by at least one 5' to 3' internucleotide linkage.

The terms "modified oligonucleotide" and "oligonucleotide analog," as used herein, encompass a molecule of ribonucleotides or deoxyribonucleotides which are covalently linked via at least one synthetic linkage. A "synthetic internucleotide linkage" is a linkage other than a phosphodiester between the 5' end of one nucleotide and the 3' end of another nucleotide in which the 5' internucleotide phosphate has been replaced with any number of chemical groups. Representative synthetic linkages include phosphorothioates, phosphorodithioates, alkylphosphonothioates, phosphoramidates, phosphate esters, carbamates, carbonates, phosphate triesters, acetamidate, and carboxymethyl esters.

The term "oligonucleotide analog" also encompasses oligonucleotides with a modified base and/or sugar. For example, a 3', 5'-substituted oligonucleotide is a modified oligonucleotide having a sugar which, at both its 3' and 5' positions is attached to a chemical group other than a hydroxyl group (at its 3' position) and other than a phosphate group (at its 5' position). A modified oligonucleotide may also be a capped species. Also encompassed by these terms are unoxidized oligonucleotides or oligomers having a substitution in one nonbridging oxygen per nucleotide in the molecule.

Oligonucleotide analogs may also be synthetic oligonucleotides" which encompasses polymers of 3' to 5'-linked ribonucleosides, 2'-modified ribonucleosides and/or deoxyribonucleosides having only as many nucleosides as are conveniently chemically synthesized (i.e., up to about 80–100). Also encompassed are those oligonucleotides having base or sugar modifications as well as those having nuclease resistance-conferring bulky substituents at their 3' and/or 5' end(s), multiple ribonucleosides and/or deoxyribonucleosides linked via an internucleotide linkage not found in native DNA, i.e., linkages other than phosphodiester bonds, or having modified bases and/or sugars in various other structural modifications not found in vivo without human intervention.

In the method of the invention, a single-stranded ligation product is prepared which includes a target oligonucleotide-to-be-sequenced and an auxiliary oligonucleotide, each having a 3' and 5' end. The auxiliary oligonucleotide has a nucleotide sequence complementary to the sequence of a primer-to-be-used. In one aspect of the invention, the auxiliary oligonucleotide also includes a signalling sequence of at least four contiguous nucleotides at its 5' end, which become inked to the 3' end of the target oligonucleotide in the ligation product. In some embodiments, the auxiliary oligonucleotide is at least eight nucleotides in length.

The invention provides several preferred methods of preparing the single-stranded ligation product depending in part upon the degree to which the sequence of the target oligonucleotide is known, If at least the last three nucleotides, and preferably six, are known, a bridge oligonucleotide is prepared which is complementary to these known nucleotides at its 5' end and which further includes a nucleotide sequence that is complementary to the first at least four 5' nucleotides of the auxiliary nucleotide. This bridge is used to anneal to the 3' end of the target oligonucleotide and the 5' end of the auxiliary nucleotide, forming a double stranded construct. The target oligonucleotide can then be ligated to the auxiliary oligonucleotide via a ligase.

A bridge is also used in another embodiment where the sequence of the target oligonucleotide is completely unknown. In this method a set of sixteen bridge oligonucleotides is prepared. Each bridge oligonucleotide is identical in part in having about six nucleotides at its 3' end which are complementary to the six nucleotides at the 5' end of the auxiliary oligonucleotide. The bridge oligonucleotides differ in having at their 5' ends a unique dinucleotide sequence (i.e., one of sixteen possible combinations of four nucleotides), one of which being complementary to the last two unknown 3' nucleotides of the target oligonucleotides). The one bridge oligonucleotide which anneals to the auxiliary and target oligonucleotides provides the same function as described above in the first bridge embodiment.

In another preferred embodiment, the method used for preparing the ligation product including a target oligonucleotide with a completely unknown sequence is as follows. An auxiliary oligonucleotide is prepared which, like those described above, is composed of a 3' sequence complementary to the sequence of a primer to be used. This sequence is linked at its 5' end to a signalling sequence of at least four known contiguous nucleotides. The 3' nucleotide of the auxiliary oligonucleotide is protected in some cases (when using RNA ligase). The 5' end of this auxiliary oligonucleotide is ligated directly to the 3' end of the target molecule. In preferred aspects of the invention, ligation is accomplished with a blunt end ligase such as $T_4$ RNA ligase.

In any case, to this ligation product is annealed a primer which has a nucleotide sequence complementary to a portion of the auxiliary oligonucleotide. In some aspects of the invention, the primer comprises a nucleotide sequence complementary to at least four, but preferably at least eight, nucleotides of the auxiliary oligonucleotide portion of the ligation product. This primer also has a label covalently attached thereto. Preferably, this label is a fluorescent, chemiluminescent, or radioactive tag. Most preferably, the label is a fluorescent label which is excitable in the UV or visible range and which fluoresces in the visible range.

Next, the primer is extended with chain-extending nucleoside triphosphates and chain-terminating nucleoside triphosphates in the presence of a polymerase to yield a plurality of primer extension products of differing lengths. These products are then separated on the basis of their relative mobilities, from which the nucleotide sequence of the target oligonucleotide can be derived. In preferred embodiments of the invention separation is achieved by slab gel or high performance capillary gel electrophoresis. Depending on the primer label used, laser-induced fluorescence, UV absorption, or radiation are measured to determine the relative mobilities of the primer extension products.

BRIEF DESCRIPTION OF THE DRAWINGS

The foregoing and other objects of the present invention, the various features thereof, as well as the invention itself may be more fully understood from the following description, when read together with the accompanying drawings in which.

BRIEF DESCRIPTION OF THE PREFERRED EMBODIMENTS

Figure 1A:
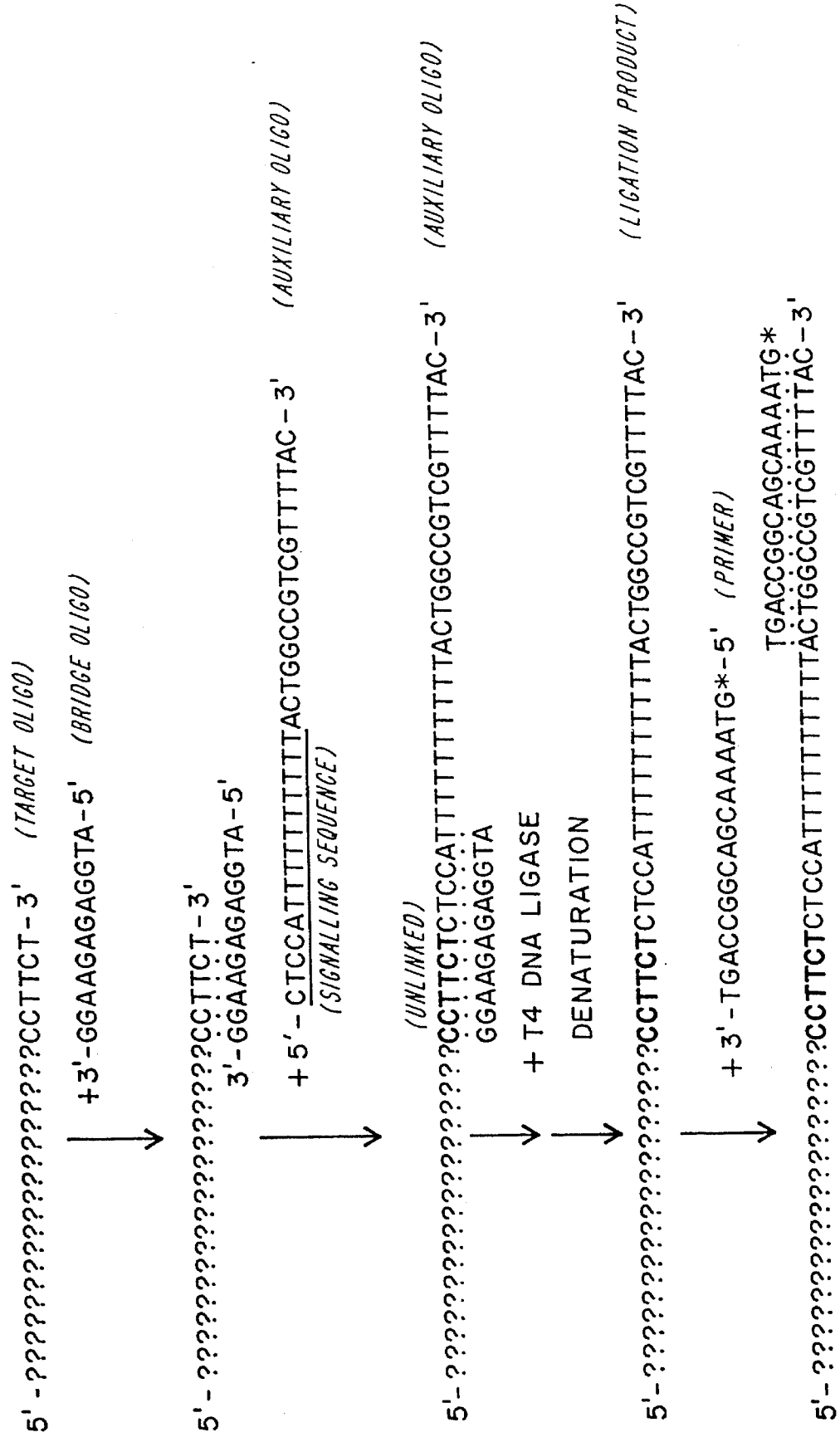
FIG. 1A is a schematic representation of one embodiment of the invention by which a single-stranded ligation product is prepared from a target oligonucleotide whose sequence is partially known.

The patent and scientific literature referred to herein establishes the knowledge that is available to those with skill in the art. The issued U.S. patent and allowed applications cited herein are hereby incorporated by reference.

This invention provides a new sequencing procedure which determines the sequence of a target oligonucleotide from its very first 5' nucleotide to its very last 3' nucleotide, despite the shortness of its length or the fact that it may be an oligonucleotide analog with non-phosphodiester internucleotide linkages and/or other modifications. In fact, any target oligonucleotide can, in principle, be sequenced.

For example, the target oligonucleotides-to-be-sequenced can range from about 4 to about 100 nucleotides in length, with oligonucleotides having from about 8 to about 50 nucleotides in length being most common. Furthermore, target oligonucleotides can have any type of internucleotide linkages or even any combination of different types of internucleotide linkages, as long as the target oligonucleotide can be ligated to the auxiliary oligonucleotide and can be extended by a polymerase. For example, a target oligonucleotide may have more than one non-phosphodiester linkage, and up to having all non-phosphodiester linkages. The non-phosphodiester linkages present in the target oligonucleotide may include at least phosphorothioate, alkylphosphonate, phosphoramidate, alkylphosphonothioate, phosphodithioate, and sulfone, sulfate, keto, phosphate ester, bridged phosphorothioate and bridged phosphoramidate linkages, all of which are known in the art (see Uhlmann et al. (1990) (*Chem. Rev.* 90:543–584 for a review on the synthesis and characteristics of phosphodiester and non-phosphodiester-linked antisense oligonucleotides).

The method of the invention requires the preparation of an "auxiliary oligonucleotide" which is used for ligation to the 3' end of the target oligonucleotide-to-be-sequenced, thereby forming a single-stranded ligation product. The auxiliary oligonucleotide is a single-stranded RNA, DNA, or RNA/DNA-containing molecule with a known sequence that is complementary to a primer. The auxiliary oligonucleotide may also include at its 5' end a region of at least four preselected, contiguous nucleotides which serves as a marker or "signalling sequence."

This auxiliary oligonucleotide is ligated to the target molecule to form a single-stranded ligation product, wherein base #1 of the target oligonucleotide-to-be-sequenced is located directly after the auxiliary DNA.

The invention provides several protocols for preparing the ligation product, depending on the degree to which the sequence of the target oligonucleotide is known. If at least the last three, and preferably six nucleotides at the 3' end of the target are known, a bridge oligonucleotide can be constructed which supports the target oligonucleotide and facilitates the ligation reaction. The bridge includes ribonucleotides and/or deoxyribonucleotides linked via phosphodiester and other than phosphodiester internucleotide linkages. This molecule is complementary to these at least six nucleotides and further includes a sequence that is complementary to the first at least four 5' nucleotides of the auxiliary nucleotide. The bridge oligonucleotide is annealed to the target oligonucleotide and to the auxiliary oligonucleotide such that the first two 3' nucleotides of the bridge oligonucleotide are annealed to the last two 3' nucleotides of the target oligonucleotide, and at least the next six nucleotides of the bridge oligonucleotide towards its 5' end are annealed to the first six 5' nucleotides of the auxiliary oligonucleotide, thereby yielding a partially double stranded construct. Then, the 3' end of the target oligonucleotide is ligated to the signalling sequence at the 5' end of the auxiliary oligonucleotide with a template-dependent enzyme such as T4 DNA ligase or Taq DNA ligase. Upon denaturation, a single-stranded ligation product is obtained.

Figure 2A:
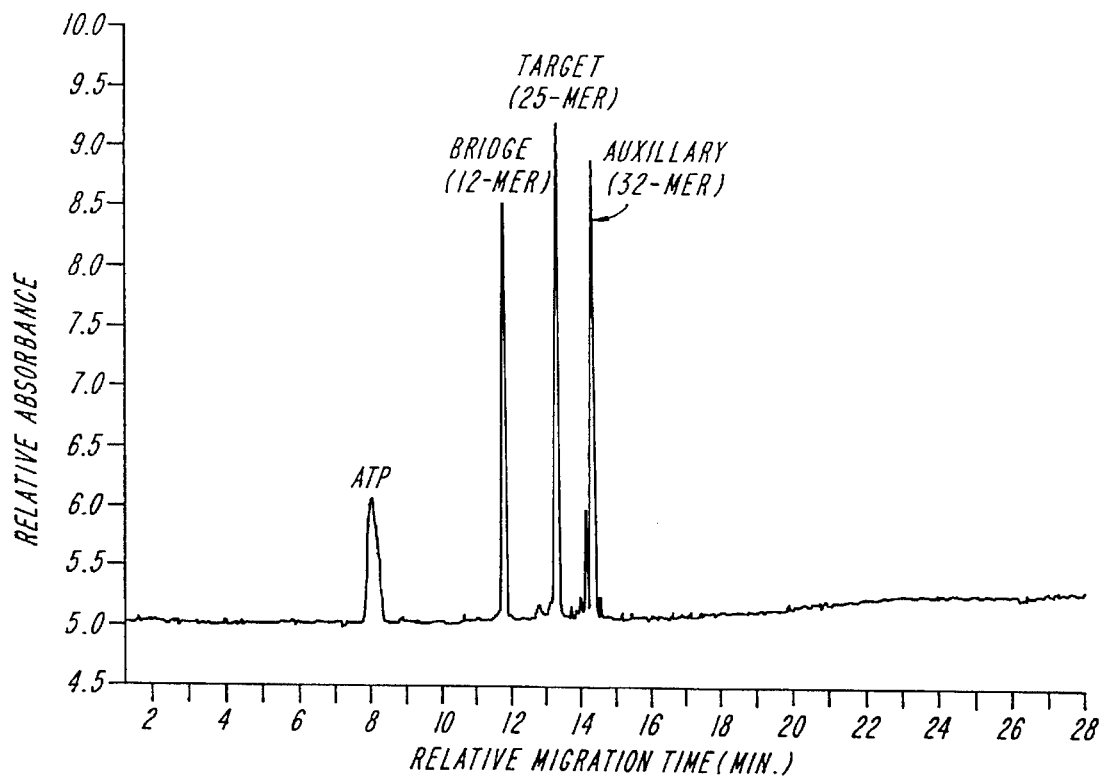
FIG. 2A is a UV electropherogram of a reaction mixture containing ATP, a 12mer bridge oligonucleotide, a 25mer target oligonucleotide whose sequence is partially known, and a 31mer auxiliary oligonucleotide.
Figure 2B:
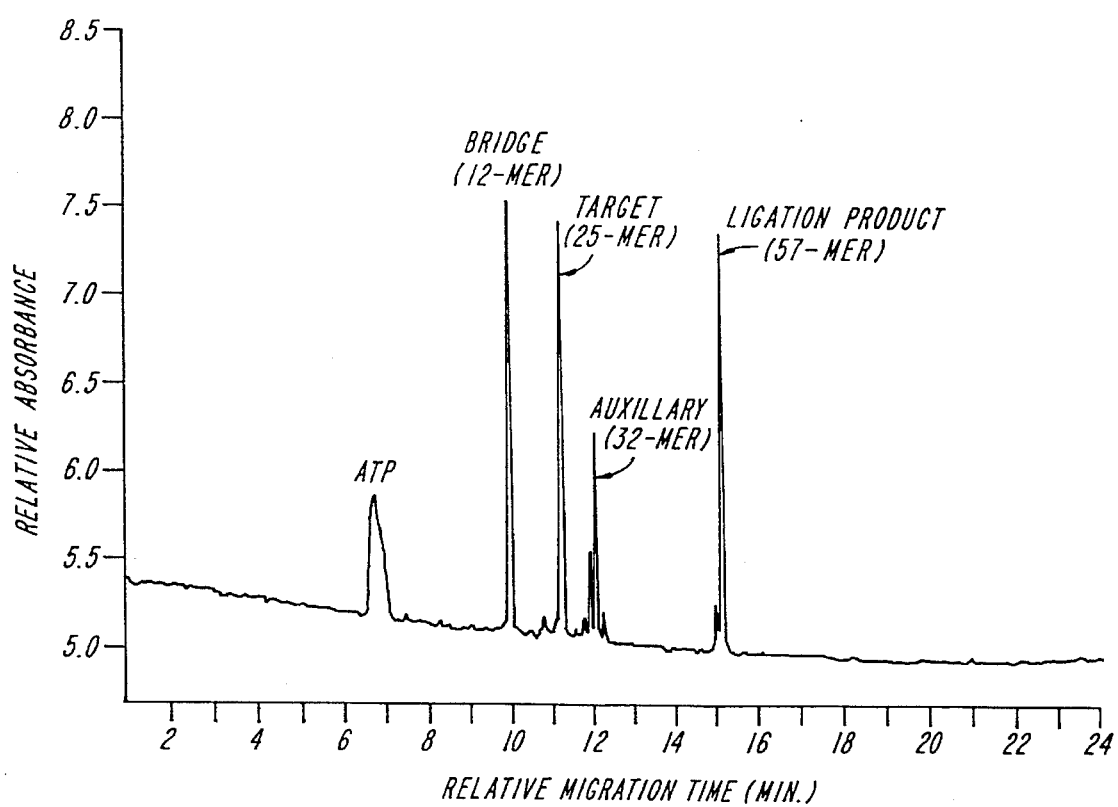
FIG. 2B is a UV electropherogram of the reaction mixture described in FIG. 2A after ligation with $T_4$ DNA ligase, and shows the species in FIG. 2A as well as a 57mer ligation product.

An example of this ligation protocol is shown schematically in FIG. 1A, where at least 3 bases of a target oligonucleotide are already known. In this figure, the bases that are unknown are depicted as "?". A 12mer bridge (SEQ ID NO:2) is prepared to facilitate the ligation of the auxiliary oligonucleotide to the target molecule. This bridge consists of two regions of six bases, one region that is complementary to the last six bases of the auxiliary oligonucleotide (SEQ ID NO:3) at its 5' end and the other being complementary to a predetermined first six bases of the target oligonucleotide at its 3' end which are known. FIGS. 2A and 2B show the separation of varies species of oligonucleotides (target, auxiliary, and bridge) by capillary electrophoresis, followed by UV detection, before and after ligation with T4 DNA ligase, respectively. Migration order of detected peaks in FIG. 2A is (1) the fast migrating 12mer bridge (SEQ ID NO:2); (2) the target oligonucleotide-to-be-sequenced; and (3) the auxiliary oligonucleotide. When T4 DNA ligase and ATP are added to the reaction mixture, after 30 minutes incubation at 37° C., a 57mer ligation product is observed (FIG. 2B).

Figure 1B:
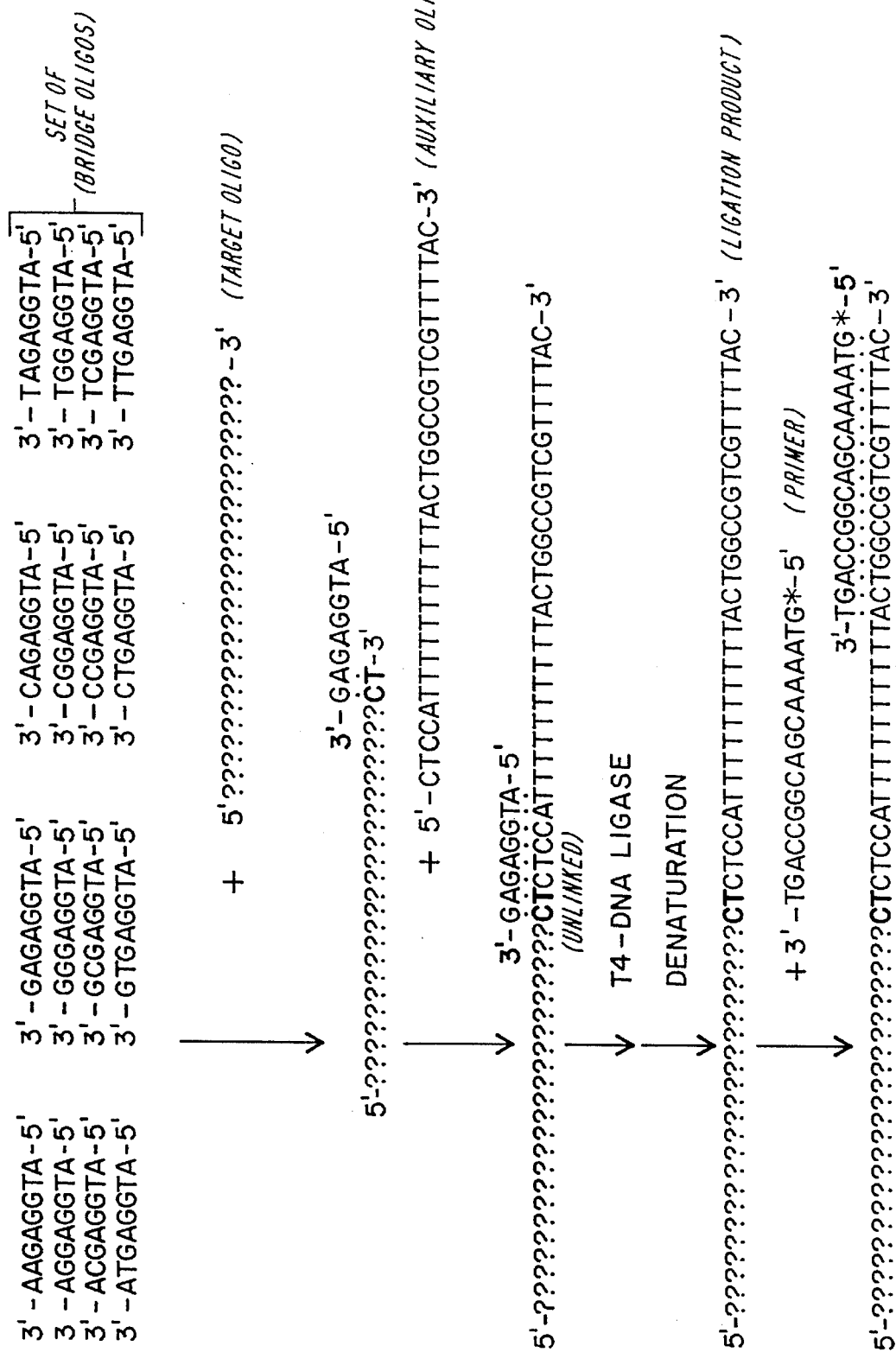
FIG. 1B is a schematic representation of another embodiment of the invention by which a single-stranded ligation product is prepared, with the aid of a bridge oligonucleotide, from a target oligonucleotide whose sequence is unknown.

If the entire sequence of the target oligonucleotide is unknown, two methods of preparing the ligation product be used. One, like the method above, also requires the support of a bridge oligonucleotide. In this method, a set of sixteen bridge oligonucleotides is prepared, all of which are identical at their 5' ends because they include a sequence complementary to the same four, but preferably six to eight or more nucleotides of an auxiliary oligonucleotide to be used. In addition, the bridge oligonucleotides include at their 3' ends one of sixteen possible dinucleotides: AA, AC, AG, AT, CA, CC, CG, CT, GA, GC, GG, GT, TA, TC, TG, TT. One of these dinucleotides will be complementary to the two most 3' nucleotides of the target oligonucleotide. Thus, when this set of sixteen bridge oligonucleotides is mixed with the target oligonucleotide of unknown sequence and with the auxiliary oligonucleotide described above, under conditions conducive for annealing, the one bridge oligonucleotide having a dinucleotide complementary to the last two 3' nucleotides of the target molecule will hybridize to it as well as to the auxiliary oligonucleotide. This method is shown schematically in FIG. 1B, where the sixteen bridge oligonucleotides have SEQ ID NOS:6–21, and each unknown base in the target oligonucleotide is depicted shown as a "?".

Alternatively, a blunt end ligase such as T4 RNA ligase may be used which does not require the presence of a double-stranded construct to link two nucleotides together. In this case, an auxiliary oligonucleotide is prepared which is composed of a 3'-sequence complementary to the sequence of a primer to be used, linked to a 5'-signalling sequence of at least four contiguous nucleotides. The 3' end of this auxiliary oligonucleotide is protected with, for example, a dideoxynucleotide (ddA, ddC, ddG, ddT) or an amino group. The 5' end of the auxiliary oligonucleotide is then ligated to the 3' end of the target oligonucleotide, thereby forming a single-stranded ligation product.

Figure 1C:
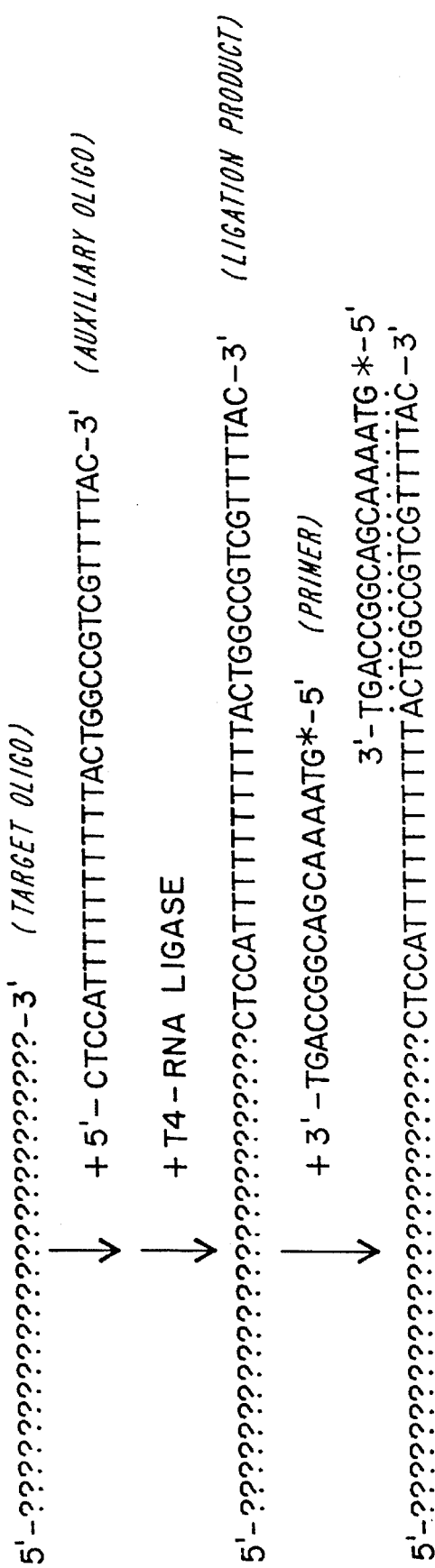
FIG. 1C is a schematic representation of yet another embodiment of the invention by which a single-stranded ligation product is prepared, without the aid of a bridge oligonucleotide, from a target oligonucleotide whose sequence is unknown.
Figure 3A:
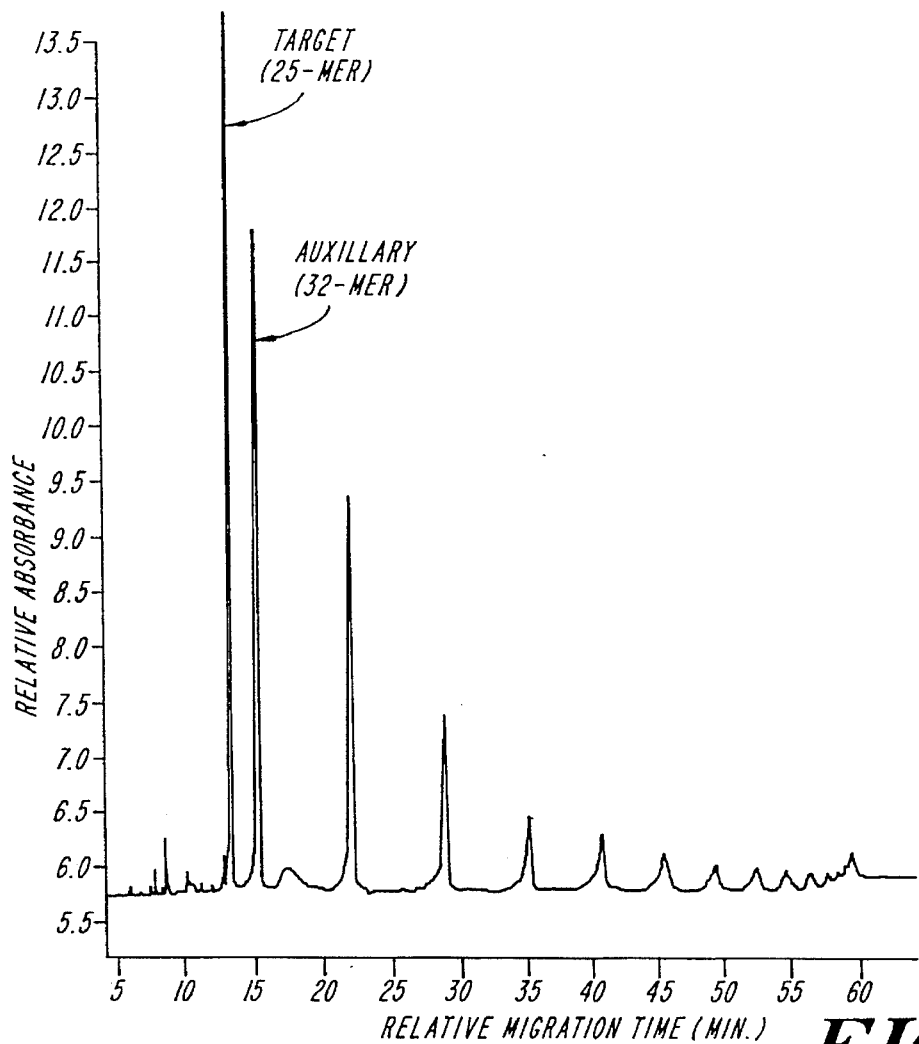
FIG. 3A is a UV electropherogram of the HPCE separation of the components of a T₄RNA ligase reaction mixture including ATP, the target oligonucleotide, and a 31mer auxiliary oligonucleotide with an unprotected 3' hydroxyl group.
Figure 3B:
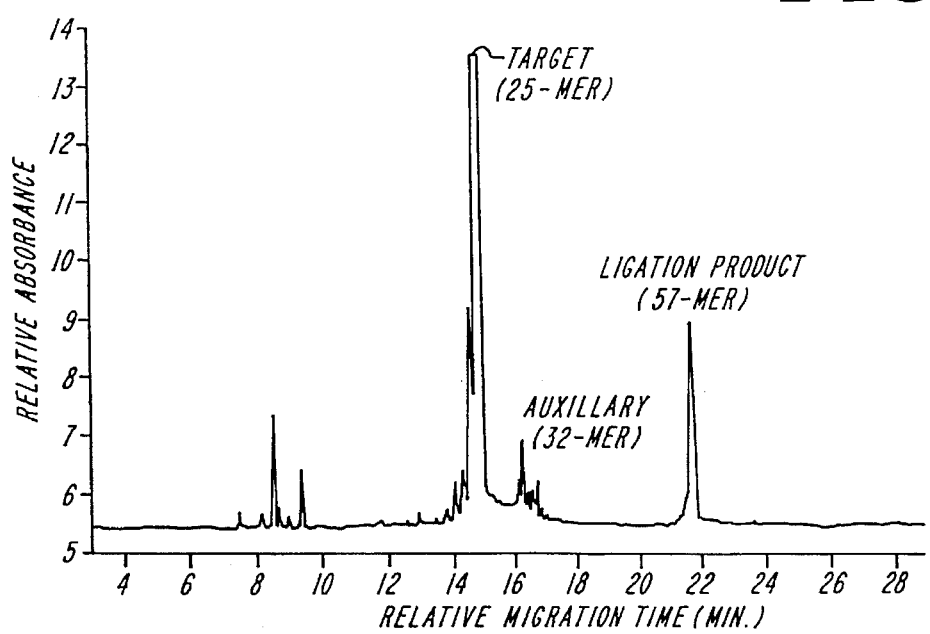
FIG. 3B is a UV electropherogram of HPCE separation of the components of a T₄RNA ligase reaction mixture as in FIG. 3A, except using a 31mer auxiliary oligonucleotide with a 3' amino protected end, and resulting in a 57mer ligation product.
Figure 4A:
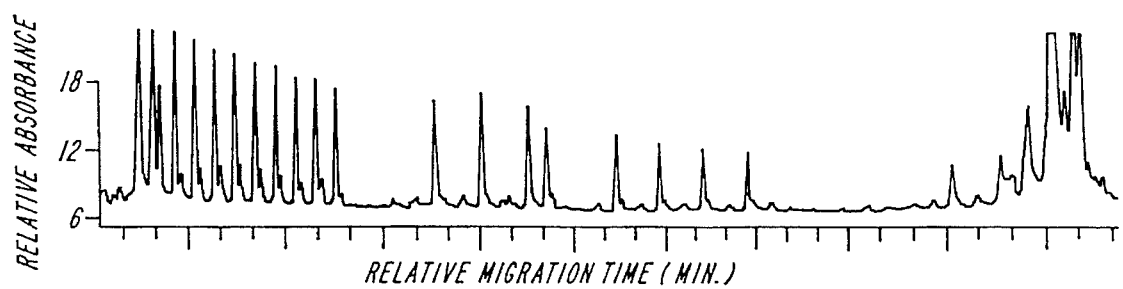
FIG. 4A is an LIF electropherogram of the HPCE separation of primer extension products made from, and complementary to, the 57mer ligation product using the ddA terminated sequencing reaction, and separated as in FIG. 2B.
Figure 4B:
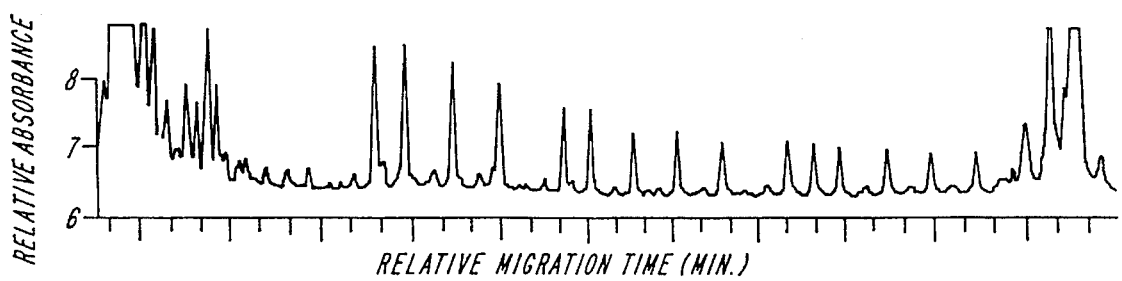
FIG. 4B is an LIF electropherogram of the HPCE separation of primer extension products made from, and complementary to, the 57mer ligation product using the ddG terminated sequencing reaction.
Figure 4C:
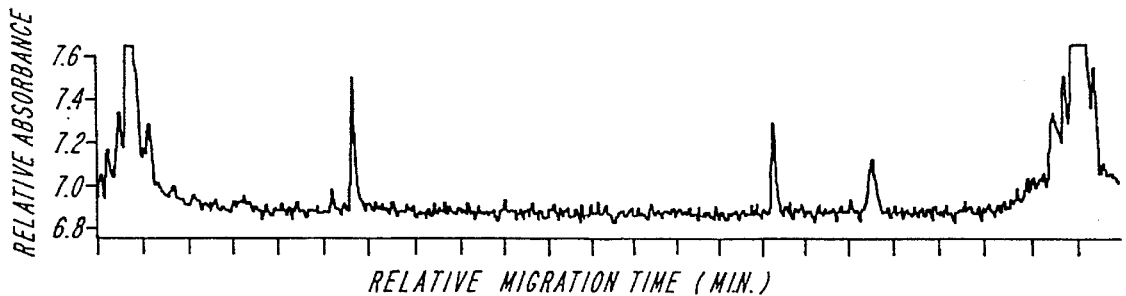
FIG. 4C is an LIF electropherogram of the HPCE separation of primer extension products made from, and complementary to, the 57mer ligation product using the ddT terminated sequencing reaction.
Figure 4D:
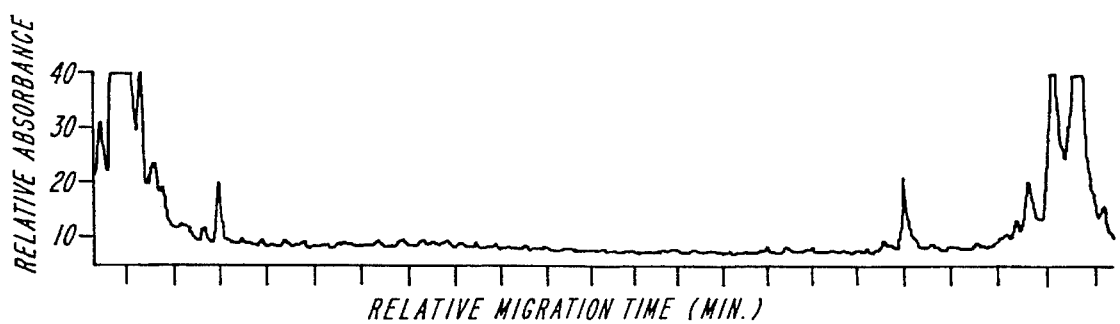
FIG. 4D is an LIF electropherogram of the HPCE separation of primer extension products made from, and complementary to, the 57mer T₄ DNA ligase ligation product using the ddC terminated sequencing reaction.

An example of this ligation protocol is shown schematically in FIG. 1C. $T_4$ RNA ligase is used to ligate a target oligonucleotide of unknown sequence to a 31mer auxiliary oligonucleotide (SEQ ID NO:3) without the presence of a bridge in the reaction mixture. The UV electropherogram shown in FIGS. 3A and 3B demonstrates the synthesis of the 57mer ligation product. If an auxiliary oligonucleotide is used having an unprotected 3' end, the enzyme forces the ligation process to proceed in cycles and several cycles are observed (FIG. 3A). This undesirable phenomenon is prevented simply by using an auxiliary oligonucleotide with a protecting dideoxy or an amino group at its 3' end, as shown in FIG. 3B where only one ligation cycle is obtained. As in the T4 RNA ligase case, the ATP 25mer analog, auxiliary-31mer, and 57mer ligation product are observed.

Once the single-stranded ligation product containing the target molecule is formed, a primer is annealed to ligation product, from which strands complementary to the target molecule can be extended by a polymerase (i.e, primer extension products). The primer oligonucleotide can be any of the conventional types of RNA and/or DNA-containing oligonucleotides that are well known and commonly used for DNA or RNA sequencing or primer extension reactions. The primer oligonucleotide has a sequence that is complementary to a 3' portion of the auxiliary oligonucleotide region of the ligation product which does not include the signalling region.

At least one molecule of a label such as a luminescent, radioactive, or fluorescent label is attached to the primer. If the label is fluorescent it is excitable in the UV or visible wavelength range, and fluoresces in the visible range. Such labels include fluorescein, or the N-succinimide ester or other derivatives thereof, such as called "JOE" (Applied Biosystems, Foster City, Calif.), "FITC" (Applied Biosystems, Foster City, Calif.), and "FAM" (Applied Biosystems, Foster City, Calif.), and rhodamine, or derivatives thereof, such as tetramethylrhodamine ("TAMARA") (Applied Biosystems, Foster City, Calif.) and "Texas Red" or "ROX" (Applied Biosystems, Foster City, Calif.) (Smith (1985) Nucl. Acid. Res. 13:2399–2412). These labels can be covalently attached to the primer, for example, by using chemical DNA or RNA synthesis as described by Smith (Am. Biolab. (1989) May:11–20), or by other methods which will not interfere with the ability of the primer to hybridize to the target molecule or to be ligated to the helper oligonucleotide. An example of one such method includes covalently attaching an amino group onto the dye and then linking the amino group 5' end of oligonucleotide (Smith (1985) Nucl. Acid. Res. 13:2399–2412). Alternatively, the fragment may be fluorescently labelled with dideoxynucleotides.

Annealing of the bridge, auxiliary, and target oligonucleotides, and of the primer and ligation product is accomplished under conditions that are most conducive for the hybridization of a single-stranded species to a complementary, single-stranded oligonucleotide. These conditions include contact in ligation buffer (600 mM Tris-HCl, pH 7.6, 66 mM $MgCl_2$, 100 mM DTT, 660 μm ATP) at a temperature of from about 4° C. to 90° C., but preferably at room temperature (i.e., 19° C. to 25° C.).

Upon annealing of the primer to the ligation product, the primer extension reaction can take place in the presence of a polymerase. Many polymerases are known in the art and all are suitable in principle. Usually, a DNA polymerase will be used such as Taq DNA polymerase or T4 DNA polymerase. If the very well known Sanger et al. (ibid.) sequencing method is to be followed, nucleotides and dideoxynucleotides are used to synthesize the primer extensions.

Finally, the dideoxy-terminated extension products are separated according to any number of well-known standard procedures that separate such molecules on the basis of size. Such protocols include polyacrylamide slab gel electrophoresis or high performance capillary gel electrophoresis. Depending on the primer label used, laser-induced fluorescence, UV absorption, or radiation are measured to determine the relative mobilities of the primer extension products.

For example, an auxiliary oligonucleotide is prepared from 17 bases at its 3' end which are complementary to the sequence of the M13mp18(–21) primer. Next is a signalling region of ten T bases. Then, base #1 of the target oligonucleotide to be sequenced is located directly 5' to the auxiliary oligonucleotide.

In developing an automated single-stranded oligonucleotide sequencer for routine antisense analysis, a working strategy was developed to examine the enzymatic sequencing of single-stranded oligonucleotide analogs which includes the ligation products described above. The following strategy was used to develop an expression for the electrophoretic migration of sequencing fragments which is an essential element of automated data processing.

Over a narrow range of molecular size, a linear relationship between relative migration time (T) and base number can be established using two internal standards in what amounts to a two-point calibration. These two points are the primer (17mer) and the 58mer fragment which is one base longer than the ligation product due to the endonuclease activity of sequenase 2.0. This linear relationship is described as follows:

$$T = \frac{Tp - Tpr}{Tfin - Tpr}$$

where "Tp" is the migration time of sequencing fragment; "Tpr" is the migration time of primer; and "Tfin" is the migration time of the last peak. This relationship is linear for T' which is only fragment size-dependent.

To validate this term, the expression was tested under experimental conditions as follows. A 57mer ligation product (SEQ ID NO:4) (e.g., a 25mer target oligonucleotide analog (SEQ ID NO:i)+a 32mer auxiliary oligonucleotide (SEQ ID NO:3)) was subjected to enzymatic chain termination reaction for four different bases independently (i.e., A, G, C, T). Each of the four reaction mixtures were run separately on different days and different gel columns. LIF electropherograms of the separation of the four sets of primer extension products are shown in FIGS. 4A–4D. Extension products were separated by HPCE using a gel containing 12% T acrylamide, 6.5 M urea, and 40% (weight-:weight) formamide. These figures are the computer two point alignments for T, G, A and C reactions. The first point is the 17mer primer and the second point is the 57mer latest migrating fragment. T' was calculated individually for each of the detected fragments between 17 and 57 bases in length. Fragment 33 corresponds to the 25mer target oligonucleotide. The obtained values are then rearranged in order form low to high, according to the occurrence in the four runs for the four individual bases in FIGS. 4A–4D. The results are summarized in TABLE 1, which is a computer printout of relative migration obtained using two point re-size alignment for the data obtained from FIGS. 4A–4D.

TABLE 1

| Base Real | Target Oligo | A | T | C | G | Reading Sequencing |
|---|---|---|---|---|---|---|
|  |  |  |  |  |  | 3' |
| 33 | 1 |  | 0.370 |  |  | T |
| 34 | 2 |  |  | 0.391 |  | C |
| 35 | 3 |  | 0.421 |  |  | T |
| 36 | 4 |  | 0.441 |  |  | T |
| 37 | 5 |  |  | 0.460 |  | C |
| 38 | 6 |  |  | 0.485 |  | C |
| 39 | 7 |  | 0.512 |  |  | T |
| 40 | 8 |  |  | 0.537 |  | C |
| 41 | 9 |  | 0.570 |  |  | T |
| 42 | 10 |  |  | 0.586 |  | C |
| 43 | 11 |  | 0.620 |  |  | T |
| 44 | 12 |  |  | 0.636 |  | C |
| 45 | 13 |  | 0.671 |  |  | T |
| 46 | 14 | 0.680 |  |  |  | A |
| 47 | 15 |  |  | 0.707 |  | C |
| 48 | 16 |  |  | 0.735 |  | C |
| 49 | 17 |  |  | 0.763 |  | C |
| 50 | 18 | 0.786 |  |  |  | A |
| 51 | 19 |  |  | 0.812 |  | C |
| 52 | 20 |  |  |  | 0.828 | G |
| 53 | 21 |  |  | 0.856 |  | C |
| 54 | 22 |  | 0.896 |  |  | T |
| 55 | 23 |  |  | 0.904 |  | C |
| 56 | 24 |  | 0.948 |  |  | T |
| 57 | 25 |  |  | 0.953 |  | C |
|  |  |  |  |  |  | 5' |

As indicated above, the sequence of the target oligonucleotide is determined in the right-most column of Table 1 from 3' to 5' end. This sequencing format is the result of computer software capable of automating the sequencing system and performing data processing.

Figure 5A:
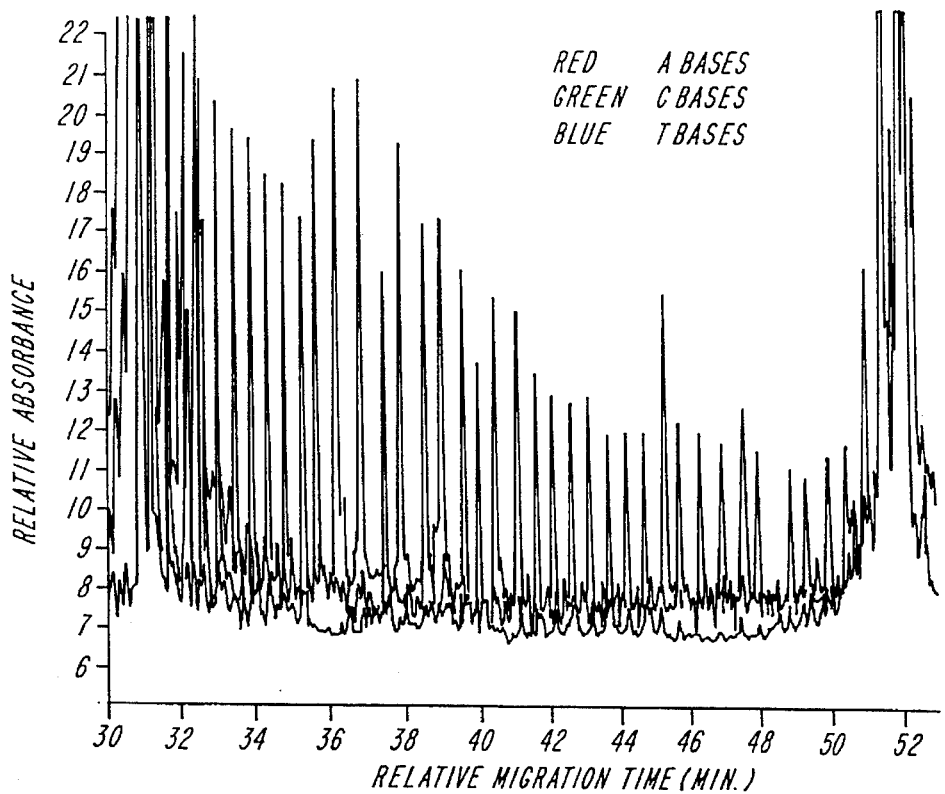
FIG. 5A is a computer overlay of the LIF electropherograms from FIGS. 4A–4C using two point re-size alignment.
Figure 5B:
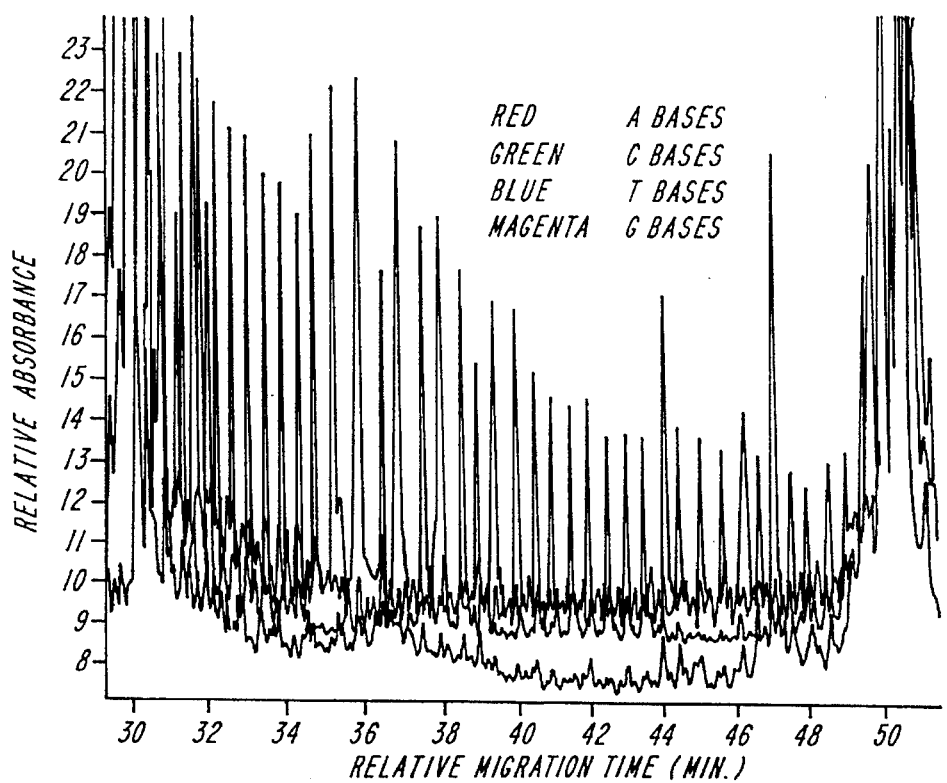
FIG. 5B is a computer overly of the LIF electropherograms from FIGS. 4A–4D, using two point re-size alignment.
Figure 6:
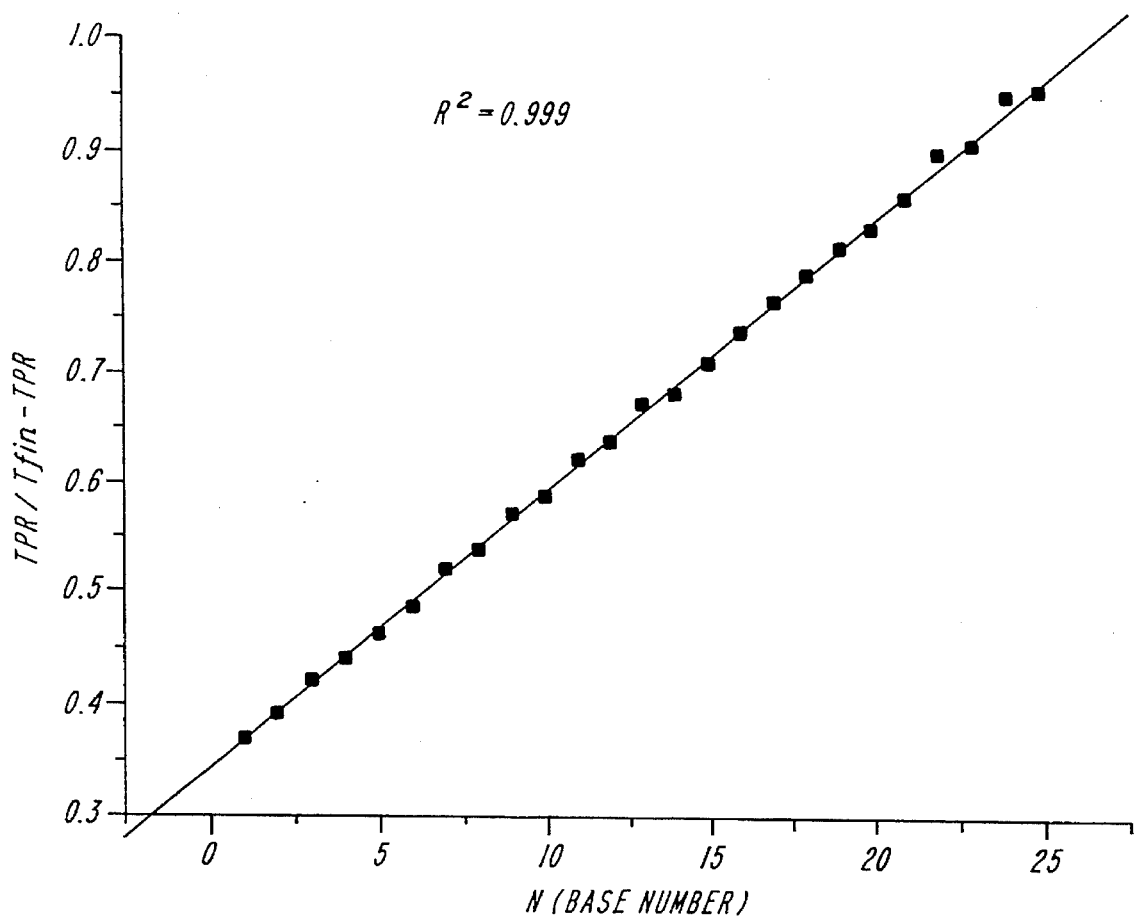
FIG. 6 is a plot of relative fragment migration versus base number for the data presented in FIGS. 5A and 5B, showing a linear relationship with $R^2=0.999$.

When this software is interfaced with a commercial software (e.g., Turbochrome™ III, P. E. Nelson, Cupertino, Calif.), the data obtained can be manipulated such that the final electropherogram of the sequencing can be plotted, as illustrated in FIGS. 5A and 5B. The results are summarized in FIG. 6 which demonstrates the linear relationship between fragment migration and base number.

Thus, a mathematical expression has been derived and successfully used for an automated single-stranded oligonucleotide sequence determination. The strength of this expression is that "T'", relates only to the fragment length expressed as base number. Moreover, this expression is independent of the experimental conditions given that all sequencing fragments are separated. Separation is not a problem, since gel capillary can separate sequencing fragments with very high efficiency and resolution (Cohen et al. (1988) *J. Chromatogr.* 458:323; Swerdlow et al. (1990) *Nucl. Acids Res.* 18:1415–1419; Pentoney et al. (1992) *Electrophoresis* 13:461–74; Cohen et al. (1993) *TRAC* 12:195–202).

The following examples illustrate the preferred modes of making and practicing the present invention, but are not meant to limit the scope of the invention since alternative methods may be utilized to obtain similar results.

EXAMPLES

1. Preparation of Target, Auxiliary, Bridge, and Primer Oligonucleotides

Phosphodiester-linked target, auxiliary, and primer oligonucleotides were synthesized by the phosphoramidite method (see McBride et al. (1983) *Tetrahedron Lett.* 24:245) using an Oligo 100™ automated DNA synthesizer (Beckman, Fullerton, Calif.). Target, auxiliary, and primer oligonucleotide analogs were synthesized by known methods (Uhlmann et al. *Analyt. Chem.* (1990) 90:543–583), and then desalted, lyophilized, and reconstituted in buffer for the sequencing protocol or in sterile water for HPCE (Lyphomed Deerfield, Ill.).

An auxiliary oligonucleotide is prepared from 17 bases at its 3' end which are complementary to the sequence of the M13mp18(–21) primer. Next is a signalling region of ten T bases. Then, base #1 of the target oligonucleotide to be sequenced is located directly 5' of the auxiliary oligonucleotide.

A 12mer bridge is prepared which consists of two regions of six bases, one region being complementary to the last six bases of the auxiliary oligonucleotide at its 5' end and the other being complementary to a predetermined first six bases of the target oligonucleotide at its 3' end.

The primer is labelled by covalently attaching a label to its 5' end. This is accomplished by phosphoramidite chemistry using an automated oligonucleotide synthesizer.

Alternatively, the primer is labelled by covalently attaching a fluorescent tag such as derivatized fluorescein ("FAM") to its 5' end by using chemical DNA or RNA synthesis as described by Smith (*Am. Biolab.* (1989) May:11–20).

2. Preparation of Ligation Product Including an Oligonucleotide With a Known Sequence About 6 µg of target oligonucleotide are mixed with 3 µg of 5'-phosphorylated auxiliary DNA, 4 µg of bridge oligonucleotide, and 5 µl 10× ligation buffer (USB 70087). The final volume is about 15 µl. This mixture is incubated at 37° C. for 15 minutes and then cooled in an ice bath at 4° C. for 20 minutes. 1 µl T4-DNA ligase (USB 70005, 300 units/µl) is then added to the mixture and kept at 37° C. for 1 hour. The ligase is inactivated at 70° C. for 5 minutes.

3. Preparation of Ligation Product Including an Oligonucleotide With an Unknown Sequence A. No Bridge Method This protocol is based on the method of Tessioer (*Analyt. Biochem.* (1986) 158:171–178). 3 μl 5× ligation buffer (50 mM $MgCl_2$, 5 mM $Co(NH_3)6Cl_3$, 250 mM Tris-HCl, pH 8, 50 mg/ml bovine serum albumin (USB 10848)) is mixed with 6 μg target oligonucleotide, 1 μg auxiliary DNA, 5 μl 50% polyethylene glycol (USB 19959), and 2 μl T4- RNA ligase (USB 21245,20,000 μn/ml). The final volume is about 15 μl. Auxiliary DNA is phosphorylated from 5' end; and amino-linked from the 3' end to eliminate the formation of side ligation reaction products including the auxiliary oligonucleotide and the primer. This mixture is incubated at 25° C. overnight.

B. Bridge Method

A set of sixteen bridge oligonucleotides are synthesized by phosphoramidite chemistry using a Beckman Oligo 100™ (Fullerton, Calif.).

Then, about 6 μg of target oligonucleotide are mixed with 3 μg of 5'-phosphorylated auxiliary DNA, 4×16=32 μg of bridge oligonucleotide, and 5 μl 10× ligation buffer (USB 70087). The final volume is about 15 μl. This mixture is incubated at 37° C. for 15 minutes and then cooled in an ice bath at 4° C. for 20 minutes. 1 μl T4-DNA ligase (USB 70005,300 units/μl) is then added to the mixture and kept at 37° C. for 1 hour. The ligase is inactivated at 70° C. for 5 minutes.

4. Primer Annealing

The single-stranded ligation product 3 μl 0.1 pM/μl was mixed with 8 μl 0.4 pM/μl primer (ABI 401131-21M13 primer) was mixed with 3 μl 0.1 pM/μl ligation product and 4 μl 5× sequencing buffer (USB 70702). The mixture is heated at 65° C. for 10 minutes and cooled slowly to room temperature for 30 minutes to allow for annealing.

5. Sequencing the Primer Extension Products by the Chain Termination Method

Primer extension/termination is accomplished as follows: 15 μl annealed mixture is mixed with 5 μl manganese buffer (USB 72600), 2 μl 0.1M dithiothreitol (USB 70726), 2 μl sequenase version 2.0 (USB 70775), and 1 μl pyrophosphates (USB 70950) in the presence of either four different mixtures containing 4 μl dNTP (2 mM each), 2 μl 0.5 mM ddATP or ddCTP or ddTNP or ddGTP, or a single mixture containing a specific ratio of dideoxynucleotides ddATP, ddCTP, ddTNP, and ddGTP (8:4:2:1) as described by Tabor and Richardson (*J. Biol. Chem.* (1990) 265:8322–8328). The mixture is incubated at 37° C. for 15 minutes and precipitated with 70% EtOH twice.

6. Separation of the Primer Extension Products by HPCE

Gel-filled capillaries are prepared as follows. Fused-silica capillary tubing (Polymicro Technologies, Phoenix, Ariz., USA) with an inner diameter of 75 μm, an outer diameter of 375 μm, an effective length of 10–15 cm, and a total length of 30–60 cm was treated with (methylacryloxypropyl) trimethoxysilane (Petrach Systems, Bristol, Pa., USA), and then filled with a de-gassed solution of 14% T polymerizing acrylamide, 7M urea in aqueous or formamide media (TBE buffer: 0.1M to 0.3M Tris-borate, 2–6 mM EDTA pH 8.3, 7M urea). Polymerization was achieved by adding ammonium persulfate solution and N, N, N', N',tetramethyl-ethylenediamine (TEMED). This protocol is based on the method of Smith et al. (Nature (1986) 321:674). The running buffer was 0.2M TBE, and the applied field was 400 V/cm.

The capillary electrophoresis apparatus with UV and laser-induced fluorescence detection for the separation of oligonucleotide sequencing fragments is the same as that described by Smith et al. (*Nature* (1986) 321:674). Briefly, a 30 kV, 500 μA direct current high voltage power supply (Model ER/DM; Glassman, Whitehouse Station, N.J., USA) is used to generate the potential across the capillary. UV detection of phosphorothioates and other analogs at 270 nm was accomplished with a spectrophotometer (Spectra 110, Spectra-Physics, San Jose, Calif.). For laser induced fluorescence detection an argon ion laser (Model 543 100BS, Omnichrom, Chino, Calif., USA) was employed. The data were acquired and stored on an AcerPower 486/33 computer (Acer American Corp., San Jose, Calif., USA) through an analog-to-digital converter (Model 970, Nelson Analytical, Cupertino, Calif., USA).

---

What is claimed is:

1. A method for determining the nucleotide sequence of a target oligonucleotide, comprising the steps of:

(a) ligating the 3' end of a target oligonucleotide-to-be-sequenced to the 5' end of an auxiliary oligonucleotide with a blunt end ligase, thereby forming a linear, single-stranded ligation product,
the auxiliary oligonucleotide being composed of a 3'-sequence complementary to the sequence of a primer to be used, linked to a 5'-signalling sequence of at least four contiguous nucleotides, the nucleotide at the 3' end being protected to prevent ligation thereto; and
wherein the ligation does not require any knowledge of the nucleotide sequence of the target oligonucleotide;

(b) annealing a primer to the auxiliary oligonucleotide portion of the ligation product, the primer having a nucleotide sequence that is fully and only complementary to at least a portion of the auxiliary oligonucleotide and having a label covalently attached thereto;

(c) extending the primer with chain-extending nucleoside triphosphates and chain-terminating nucleoside triphosphates in the presence of a polymerase to yield a plurality of primer extension products;

(d) separating the primer extension products on the basis of their base length; and (e) determining the nucleotide sequence of the target oligonucleotide from mobilities of the primer extension products obtained during their separation.

2. The method of claim 1 wherein ligating step (a) comprises ligating the auxiliary oligonucleotide to the target oligonucleotide with T4 RNA ligase.

3. A method for determining the nucleotide sequence of a target oligonucleotide, comprising the steps of:

(a) ligating the 3' end of a target oligonucleotide-to-be-sequenced to the 5' end of an auxiliary oligonucleotide, the ligating step further comprising:
   (i) preparing an auxiliary oligonucleotide composed of a sequence complementary to the sequence of a primer;
   (ii) preparing a set of sixteen bridge oligonucleotides, each bridge oligonucleotide including the same six nucleotides at its 5'-end which are complementary to six nucleotides at the 5'-end of the auxiliary oligonucleotide and two nucleotides at its 3'-end which have one of sixteen different possible sequences, one of which is complementary to the last two 3' nucleotides of the target oligonucleotide;
   (iii) annealing the auxiliary and target oligonucleotides to the bridge oligonucleotide with the two 3' nucleotides complementary to the last two 3' nucleotides of the target molecule, such that the first two 3' nucleotides of the bridge oligonucleotide hybridize to the last two 3' nucleotides of the target oligonucleotide, and the next six nucleotides of the bridge oligonucleotide at its 5' end hybridize to the first six 5' nucleotides of the auxiliary oligonucleotide; and
   (iv) ligating the 3' end of the target oligonucleotide to the signalling sequence at the 5' end of the auxiliary oligonucleotide, thereby forming a single-stranded ligation product;
   wherein the ligation does not require any knowledge of the nucleotide sequence of the target oligonucleotide;

(b) annealing a primer to the auxiliary oligonucleotide portion of the ligation product, the primer having a nucleotide sequence that is fully and only complementary to at least a portion of the auxiliary oligonucleotide and having a label covalently attached thereto;

(c) extending the primer with chain-extending nucleoside triphosphates and chain-terminating nucleoside triphosphates in the presence of a polymerase to yield a plurality of primer extension products;

(d) separating the primer extension products on the basis of their base length; and (e) determining the nucleotide sequence of the target oligonucleotide from mobilities of the primer extension products obtained during their separation.

4. The method of claim 3 wherein ligating step (a) comprises preparing a bridge oligonucleotide including nucleotides selected from the group consisting of ribonucleotides, deoxyribonucleotides, analogs of ribonucleotides, analogs of deoxyribonucleotides, and combinations thereof.

5. The method of claim 3 wherein ligating step (a) comprises preparing a bridge oligonucleotide comprising internucleotide linkages selected from the group consisting of phosphodiester, phosphorothioate, alkylphosphonothioate, phosphorodithioate, phosphoramidate, phosphate ester, phosphate triesters, carbamates, carbonates, acetamidate, carboxymethyl esters, and combinations thereof.

6. The method of claim 3 wherein ligating step (a) comprises preparing a bridge oligonucleotide comprising a dinucleotide at its 3'-end selected from the group consisting of AA, AT, AC, AG, TA, TT, TC, TG, CA, CT, CC, CG, GA, GT, GC, and GG.

7. The method of claim 1 or 3, wherein annealing step (b) comprises annealing a primer complementary to the ligation product, the primer comprising a nucleotide sequence complementary to at least four nucleotides of the auxiliary oligonucleotide portion of the ligation products.

8. The method of claim 1 or 3, wherein annealing step (b) comprises annealing a primer to the ligation product, the primer including nucleotides selected from the group consisting of ribonucleotides, deoxyribonucleotides, analogs of ribonucleotides, analogs of deoxyribonucleotides, and combinations thereof.

9. The method of claim 1 or 3, wherein annealing step (b) comprises annealing a primer to the ligation product, the primer including internucleotide linkages selected from the group consisting of phosphodiester, phosphorothioate, alkylphosphonothioate, phosphorodithioate, phosphoramidate, phosphate ester, phosphate triesters, carbamates, carbonates, acetamidate, carboxymethyl esters, and combinations thereof.

10. The method of claim 1 or 3, wherein annealing step (b) comprises annealing a primer to the ligation product, the primer having a label selected from the group consisting of a fluorescent, chemiluminescent, or radioactive tag.

11. The method of claim 10 wherein annealing step (b) comprises annealing a primer having a fluorescent label which is excitable in the UV or visible range and which fluoresces in the visible range.

12. The method of claim 1 or 3, wherein extending step (c) comprises extending the primer with a polymerase selected from the group consisting of T4 DNA ligase, T4 RNA ligase, and Taq DNA ligase.

13. The method of claim 1 or 3, wherein extending step (c) comprises extending the primer with chain terminating nucleotide triphosphates selected from the group consisting of dideoxyadenine, dideoxyguanidine, dideoxythymidine, and dideoxycytosine.

14. The method of claim 1 or 3, wherein separating step (d) comprises separating the primer extension products by slab gel or high performance capillary gel electrophoresis.

15. The method of claim 1 or 3, wherein determining step (e) comprises the use of laser induced fluorescence, UV absorption, or radiation detection to measure the relative mobilities of the primer extension products.

16. The method of claim 1 or 3, wherein the target oligonucleotide includes nucleotides selected from the group consisting of ribonucleotides, deoxyribonucleotides, analogs of ribonucleotides, analogs of deoxyribonucleotides, and combinations thereof.

17. The method of claim 1 or 3, wherein the target oligonucleotide comprises internucleotide linkages selected from the group consisting of a phosphodiester, phosphorothioate, alkylphosphonothioate, phosphorodithioate, phosphoramidate, phosphate ester, phosphate triesters, carbamates, carbonates, acetamidate, carboxymethyl esters, and combinations thereof.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:1:

CTCTCGCACC CATCTCTCTC CTTCT    2 5

( 2 ) INFORMATION FOR SEQ ID NO:2:

( i ) SEQUENCE CHARACTERISTICS:
          ( A ) LENGTH: 12 base pairs
          ( B ) TYPE: nucleic acid
          ( C ) STRANDEDNESS: single
          ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

GGAAGAGAGG TA                                                       12

( 2 ) INFORMATION FOR SEQ ID NO:3:

( i ) SEQUENCE CHARACTERISTICS:
          ( A ) LENGTH: 32 base pairs
          ( B ) TYPE: nucleic acid
          ( C ) STRANDEDNESS: single
          ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

CTCCATTTTT TTTTTACTGG CCGTCGTTTT AC                    32

( 2 ) INFORMATION FOR SEQ ID NO:4:

( i ) SEQUENCE CHARACTERISTICS:
          ( A ) LENGTH: 57 base pairs
          ( B ) TYPE: nucleic acid
          ( C ) STRANDEDNESS: single
          ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

CTCTCGCACC CATCTCTCTC CTTCTCTCCA TTTTTTTTTT ACTGGCCGTC      50

GTTTTAC                                                                               57

( 2 ) INFORMATION FOR SEQ ID NO:5:

( i ) SEQUENCE CHARACTERISTICS:
          ( A ) LENGTH: 16 base pairs
          ( B ) TYPE: nucleic acid
          ( C ) STRANDEDNESS: single
          ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

TGCCGCCAGC AAAATG                                                16

( 2 ) INFORMATION FOR SEQ ID NO:6:

( i ) SEQUENCE CHARACTERISTICS:
               ( A ) LENGTH: 8 base pairs
               ( B ) TYPE: nucleic acid
               ( C ) STRANDEDNESS: single
               ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

AAGAGGTA                                                                                    8

( 2 ) INFORMATION FOR SEQ ID NO:7:

( i ) SEQUENCE CHARACTERISTICS:
               ( A ) LENGTH: 8 base pairs
               ( B ) TYPE: nucleic acid
               ( C ) STRANDEDNESS: single
               ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

AGGAGGTA                                                                                    8

( 2 ) INFORMATION FOR SEQ ID NO:8:

( i ) SEQUENCE CHARACTERISTICS:
               ( A ) LENGTH: 8 base pairs
               ( B ) TYPE: nucleic acid
               ( C ) STRANDEDNESS: single
               ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

ACGAGGTA                                                                                    8

( 2 ) INFORMATION FOR SEQ ID NO:9:

( i ) SEQUENCE CHARACTERISTICS:
               ( A ) LENGTH: 8 base pairs
               ( B ) TYPE: nucleic acid
               ( C ) STRANDEDNESS: single
               ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

ATGAGGTA                                                                                    8

( 2 ) INFORMATION FOR SEQ ID NO:10:

( i ) SEQUENCE CHARACTERISTICS:
               ( A ) LENGTH: 8 base pairs
               ( B ) TYPE: nucleic acid (C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

GAGAGGTA 8

(2) INFORMATION FOR SEQ ID NO:11:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

GGGAGGTA 8

(2) INFORMATION FOR SEQ ID NO:12:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

GCGAGGTA 8

(2) INFORMATION FOR SEQ ID NO:13:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

GTGAGGTA 8

(2) INFORMATION FOR SEQ ID NO:14:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: cDNA (i i i) HYPOTHETICAL: NO (i v) ANTI-SENSE: NO (x i) SEQUENCE DESCRIPTION: SEQ ID NO:14:

CAGAGGTA 8

(2) INFORMATION FOR SEQ ID NO:15:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:15:

CGGAGGTA 8

(2) INFORMATION FOR SEQ ID NO:16:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:16:

CCGAGGTA 8

(2) INFORMATION FOR SEQ ID NO:17:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:17:

CTGAGGTA 8

(2) INFORMATION FOR SEQ ID NO:18:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO ( x i ) SEQUENCE DESCRIPTION: SEQ ID NO:18:

TAGAGGTA                                                                8

( 2 ) INFORMATION FOR SEQ ID NO:19:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:19:

TGGAGGTA                                                                8

( 2 ) INFORMATION FOR SEQ ID NO:20:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:20:

TCGAGGTA                                                                8

( 2 ) INFORMATION FOR SEQ ID NO:21:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:21:

TTGAGGTA                                                                8